US005683249A

United States Patent [19]
Ibsen et al.

[11] Patent Number: 5,683,249
[45] Date of Patent: Nov. 4, 1997

[54] DENTAL IMPLANT PROCESS AND TREATED PROSTHETIC

[75] Inventors: Robert L. Ibsen, Santa Maria; William R. Glace, Orcutt; Donald R. Pacropis, deceased, late of Santa Maria, all of Calif., by Irene J. Pacropis, executrix

[73] Assignee: Den-Mat Corporation, Santa Maria, Calif.

[21] Appl. No.: 408,581

[22] Filed: Mar. 22, 1995

[51] Int. Cl.$^6$ .................................................. A61C 13/08
[52] U.S. Cl. .................................. 433/201.1; 433/173
[58] Field of Search ........................ 433/172, 173, 433/174, 175, 176, 201.1; 623/16, 22, 23

[56] References Cited

U.S. PATENT DOCUMENTS

| Re. 34,937 | 5/1995 | Ibsen et al. | 106/35 |
|---|---|---|---|
| 4,156,067 | 5/1979 | Gould | 528/73 |
| 4,674,980 | 6/1987 | Ibsen et al. | 433/228.1 |
| 4,738,722 | 4/1988 | Ibsen et al. | 106/35 |
| 4,838,795 | 6/1989 | Draenert | 434/274 |
| 4,919,665 | 4/1990 | Homsy | 623/18 |
| 4,936,852 | 6/1990 | Kent et al. | 623/18 |
| 4,964,911 | 10/1990 | Ibsen et al. | 106/35 |
| 5,047,054 | 9/1991 | Vijayan et al. | 623/16 |
| 5,116,372 | 5/1992 | Laboureau | 623/13 |
| 5,151,453 | 9/1992 | Ibsen et al. | 522/14 |
| 5,334,625 | 8/1994 | Ibsen et al. | 523/115 |
| 5,336,465 | 8/1994 | Matsunaga et al. | 419/2 |
| 5,360,770 | 11/1994 | Chadwick | 501/24 |
| 5,447,966 | 9/1995 | Hermes et al. | 523/113 |

OTHER PUBLICATIONS

Galan, D., "Clinical Application of Geristore Glass–Ionomer Restorative in Older Dentitions", Journal of Esthetic Dentistry, vol. 3, No. 6, Nov.–Dec. 1991, pp. 221–226.
Pacropis, et al., Current Geristore® Research, "Studies On A Fluoride Releasing Adhesive To Various Substrates" Abstract #1703, Int'l Assoc. for Dental Research/American Association for Dental Research, 1991 Gen. Session, Acapulco, Mexico, 1 sheet.

The Dental Advisor, "Temporization," vol. 9, No. 1, Mar. 1992, 8 pages.
Wieczkowski, et al., "Microleakage Evaluation in Amalgam Restorations Used With Bases," Journal of Esthetic Dentistry, vol. 4, No. 2, Mar./Apr. 1992, pp. 37–40.
Clinical Research Associates Newsletter, Subject: Glass Ionomer–Resin–State–Of–The–Art vol. 17, Issue 3, Mar. 1993, 4 pages.
Scherer et al., "New Subgingival Restorative Procedures With Geristore® Resin Ionomer," Practical Periodontics And Aesthetic Dentistry Supplement, Jan./Feb. 1995, 6 pages.
Insert, "Geristore Fluoride–Releasing Restorative", printed by Den–Mat Corporation Jan. 1994, 1 sheet.
Insert, "Instroducing Geristore Multi–Shade Kit" printed by Den–Mat Corporation Mar. 1994, 1 sheet.
Insert, "Geristore Solutions, Geristore Bonding Restorative," printed by Den–Mat Corporation, Nov. 1991, 1 sheet.

(List continued on next page.)

*Primary Examiner*—Nicholas D. Lucchesi
*Attorney, Agent, or Firm*—Dorsey & Whitney LLP

[57] ABSTRACT

In the process of implanting a metal dental prosthesis into or on the alveolar bone, to provide anchorage or stabilization either to a tooth or to another prosthesis, which involves surgical exposure of the alveolar bone, providing means for (a) fixing a metal implant in the alveolar bone, and (b) fixing the metal implant to either a tooth or to the other prosthesis, and closing the exposure of the alveolar bone, the improvement which comprises including in respect to such means the step of applying to one or more portions of the implant or to the locus of the implant in the alveolar bone, a primary coating comprising a crosslinked resin that (i) optionally contains leachable fluoride and (ii) is biocompatible with osseous and non-osseous tissue, to effect direct bonding of the implant to the tooth or to the prosthesis, or to bone or to non-osseous tissue or a combination of them. A treated prosthetic is also described.

34 Claims, 4 Drawing Sheets

OTHER PUBLICATIONS

Insert, "Tenure Solutions, Tenure All Surface Bonding System," printed by Den-Mat Corporation Mar. 1993.

Instruction Sheet, Tenure® All-Surface Bonding System, printed by Den-Mat Corporation Sep. 1993, 1 sheet.

Insert, Tenure®, 1995, 1 sheet.

Hydron®Wound Dressing brochure, 1986, Acme/Chaston, Dayville, CT 06241, 10 pages.

CUMULATIVE FLUORIDE RELEASE
mg/mm$^2$
550 DAYS

DENTAL IMPLANT PROCESS AND TREATED PROSTHETIC

BRIEF DESCRIPTION OF THE INVENTION

A process of treating a metal dental implant inserted into or placed on the alveolar bone, in order to provide anchorage or stabilization either to teeth or to a prosthesis, which involves the improvement of applying to one or more portions of the implant or to the locus of the implant in the alveolar bone, a special biocompatible crosslinked resin that optionally contains leachable fluoride, to effect direct bonding of the implant to teeth or to a prosthesis, or to bone or to non-osseous tissue or a combination of them. The invention relates as well to the treated prosthetic.

BACKGROUND TO THE INVENTION

Geristore™ and Tenure™, sold by Den-Mat Corporation, Santa Maria, Calif., are promoted for certain uses in dentistry. U.S. Pat. Nos. 4,738,722, 5,334,625 and 5,151,453, incorporated herein by reference, describe Geristore™. Geristore™ is a small particle composite that contains fluoride, is radiopaque and hydrophilic. It has low-cure shrinkage, low coefficient of thermal expansion and high strength. It aggressively bonds by chemical coupling to dentin, enamel, composites used in dentistry, porcelain and metal, such as stainless steel. It is a paste/paste formulation that is easy to mix. It is capable of rapid cure by exposure to room temperature and for more rapid cure, by exposure to light. In addition, though it contains a fluoride, which could be toxic when ingested in large dosages, it is biocompatible and safe to use within a human or other animal when applied topically.

Tenure™ is a solvent based crosslinkable acrylic resin, provided as a solution/solution formulation. Its composition is described in U.S. Pat. No. 4,964,911, patented Oct. 27, 1990, and more effectively disclosed in allowed copending application Ser. No. 965,102, filed Oct. 22, 1992, to issue as U.S. Pat. No. Re 34,937, the disclosure of which is incorporated by reference. It is not an ionomer and does not release fluoride ion. It is less hydrophilic than Geristore™. It too is a crosslinkable resin. It contains a volatile solvent (typically acetone), which readily evaporates. After evaporation, a film of the resin rapidly cures in situ. Tenure™ bonds by chemical coupling to dentin, enamel, porcelain, metal and the composites typically used in dentistry. It has been recommended for use with Geristore™ in chemically bonding Geristore™ to dentin or enamel.

Dental implantation, i.e., oral implantation, involves the insertion a prosthesis in bone or the fixing of a prosthesis to bone. The implant is typically a metal pin, blade or casting inserted into or placed on the alveolar bone in order to provide anchorage or stabilization either to teeth or to a prosthesis. Anchorage of the prosthesis in bone is dependent on bone growth around and through the prosthesis, and/or the presence of threading in the prosthesis that forms a complementary threading in the bone. Many prosethesis used in dental implantation are screwed into the bone. A prosthesis, in the context of dental implants, includes the device that anchors or stabilizes (e.g., metal pin, blade or casting) and the device that is so anchored or stabilized. The latter device can be an acrylic resin or composite material (e.g., a filled resin) crafted (by molding, shaping, etc.) into the shape of a tooth or a set of teeth. An endodontic implant comprises a metal pin or post extending through the root canal into the periapical bone to lengthen and strengthen a pulpless tooth. An Endosteal (endosseous) [i.e., the thin layer of cells lining the medullary cavity of a bone] implant is an implant, usually of metal, introduced into the maxilla or mandible so that part of it protrudes into the mouth. The implant consists of three parts: a.) the body which is placed in the bone. b.) the abutment, which is visible in the mouth and supports and/or retains the prosthesis (or superstructure) and c.) the superstructure to which other components are attached. An implantation denture employs a prosthesis which obtains its stability and retention from a substructure lying under the soft tissues of the denture-bearing area, and which projects through the gingival tissues, e.g., subperiosteal, blade, or pin. A subperiosteal implant is an implant that conforms to the bone surface of the jaw, and is covered with mucoperiosteum, having abutments exposed in the mouth on which bridges, dentures, etc. may be fixed. An implantation denture substructure is a metal framework lying in contact with, or embedded in, bone. Projections from it pass through the mucoperiosteum to support an implant denture. The Osseointergraded implant is an implant in which there exists a direct connection between its surface and the host bone. A diodontic implant is a sterile metal rod placed in a root canal and extending through the root apex with the intention of stabilizing a tooth, especially one with a short root. It is often referred to an endodontic implant. Mandibular staple implant is a modified endosseous implant in which the metal appliance passes through the entire height of the mandible in the anterior region where posts pierce the oral mucosa in order to give fixation points to a suitable superstructure.

Cements have been employed in this procedure, but they are not favored for one reason or another.

Great stresses are put upon such protheses that are employed in implant procedures. Many of the prosthesis implanted into the alveolar bone are mechanically bonded to the bone. A metal (e.g., steel, titanium, and their alloys) pin that is threaded into the alvaleor bone depends on bone growth to and about the pin in order to fix (stabilize) it to the bone. It would be desirable to employ an adhesive to facilitate adhesion of the pin to bone. One reason for the inadequacies of some adhesives has been their inability to provide a strong enough bond between bone and the prosthesis. Another reason is that an effective bonding cement is often bioincompatible to the bone and any soft tissue associated with the implantation procedure. As a result, adhesives can generate an adverse reaction, possibly to the extent that bone growth is inhibited and the growth about the prosthesis is inhibit, thereby impairing the strength of the implant.

Though the occurrence of an adverse tissue response to an implant is low, there are times when an implant can induce such a response For example, metals or other foreign materials used in implants may induce, e.g, tissue infection, fibrous tissue bonding to the implant, an epithelial inversion around the neck of implant resulting in tissue inflammation, and the like. Frequently, such adverse tissue response is a result of overheated bone, or a lack of compatibility of the patient's bone or blood to the implant material. Even the most biocompatible metal, titanium, employed as an implant, can, under certain circumstance, cause an adverse tissue response. It would be desirable to treat such implants so that they are totally biocompatible with any tissue surface that they contact, thereby eliminating even the potential for such adverse tissue response.

THE INVENTION

This invention relates to dental implantation as described above. More particularly, the invention relates to an improvement in the process of treating a metal dental implant inserted into or placed on the alveolar bone, to provide anchorage or stabilization either to teeth or to a prosthesis. The process includes in the traditional steps of dental implantation, the application to one or more portions of the implant or to the locus of the implant in the alveolar bone, of a special biocompatible crosslinked resin that optionally contains leachable fluoride, to effect direct bonding of the implant to teeth or to a prosthesis, or to bone or to non-osseous tissue or a combination of them.

More specifically, the invention includes in the process of implanting a metal dental prosthesis into or on the alveolar bone, to provide anchorage or stabilization either to a tooth or to another prosthesis, which involves surgical exposure of the alveolar bone, providing means for (a) fixing a metal implant in the alveolar bone, and (b) fixing the metal implant to either a tooth or to the other prosthesis, and closing the exposure of the alveolar bone to effect normal healing of the surgically affected site, the improvement which comprises including in respect to such means the step of applying to one or more portions of the implant or to the locus of the implant in the alveolar bone, a crosslinked resin that (i) optionally contains leachable fluoride and (ii) is biocompatible with osseous and non-osseous tissue, to effect direct bonding of the implant to the tooth or to the prosthesis, or to bone or to non-osseous tissue or a combination of them.

This invention relates to the improvement in the process of implanting a dental prosthetic into or on bone by using a certain biocompatible adhesive that materially improves the bonding strength of the prosthetic to bone. It has been found that a particular adhesive can be applied to a prosthetic device that is inserted into or placed on the alveolar bone, to provide maximum biocompatibility and superior adhesion of the prosthetic device to bone and surrounding tissue.

The invention relates to an improved implantation process that is distinctive because it involves the step of coating at least one of (a) a dental prosthetic to be implanted in or on the alveolar bone and (b) the locus in the alveolar bone where the prosthetic is to be implanted, with a) a tenaciously-bonded hydrophilic water insoluble crosslinked resin coating (hereinafter called "the primary coating"), b) that optionally contains a measurable amount of a water/fluid leachable fluoride capable of (a) being leached from the coating in a metered amount, and (b) transporting a small amount of leached fluoride from the coating into the bone and associated soft tissue (hereinafter called "the primary coating with fluoride").

In one aspect, the invention encompasses a process that enhances normal alveolar bone growth impacted by the insertion of a metal prosthetic device in the bone during dental implantation of the prosthetic. In addition, because of the biocompatibility and adhesive qualities of the treatment, a prosthetic device (typically made of metal, ceramic or plastic) is more stably bonded to the alveolar bone and to associated soft tissue which the prosthetic comes into contact.

The invention relates to a metal dental implant prosthesic as described herein that contains, on at least a portion of thereof, a layer of the primary coating with or without fluoride whereby the implant is biocompatible to tissue that it might contact in or during implantation. In the preferred embodiment, the primary coating on the prosthetic contains fluoride.

The amount of fluoride provided in the primary coating is insufficient to cause fluorosis or any other toxic reaction, and, by processes unknown, except possibly antimicrobial processes, the fluoride assists the normal processes of bone and tissue growth.

The invention also encompasses in these dental implantation processes, the use of a composite layering of a strongly adhesively-bonded crosslinkable acrylic resin, possessing less hydrophilicity than the primary coating with or without fluoride, that rapidly in situ cures on an application surface, the bone and/or prosthetic surface, to function as a primer (hereinafter called the "primer coating") for the primary coating with or without fluoride that is applied to the same surface(s). The biocompatibility of the primary coating on the surface, bone and/or prosthetic device over the primer coating enhances healing, the adhesion of the bone to bone and bone to softer tissue, and prosthetic device to bone or softer tissue, and precludes or minimizes bone or softer tissue rejection to the surgical implantation procedure.

The primary coating comprises a resin based on an ethylenically unsaturated-functional monomer that contains a hygroscopic group. The ethylenically-unsaturated-functional monomer contains hygroscopic groups and exhibits hydrophilicity. Typical of such groups are hydroxyl, amide, amine, aliphatic ether, amine, hydroxyalkyl amine, hydroxyalkyl amide, pyrrolidone, ureyl, and the like.

Another ingredient of the primary coating composition is a polycarboxylic acid, i.e., a polymer that contains pendant carboxyl groups. The polycarboxylic acid is thought to enhance bonding of the primary coating resins to metallic and other substrates, particularly to organic and inorganic salt forming materials that are present in the substrate to which the primary coating is applied. In addition, the polycarboxylic acid enhances the bonding of the resin components of the primary coating composition to any inorganic fillers provided in the coating formulation. In a number of contemplated uses for the primary coating, in accordance with this invention, the polycarboxylic acid may be excluded from the primary coating formulation. In addition, one may employ the alkali metal salt of the polycarboxylic acid.

In addition, the primary coating contains a variety of crosslinking agents. One type of crosslinking agent is "hard crosslinker" and another is a "soft crosslinker." Both hard and soft crosslinker are polyfunctional molecules in which the functionality is complementary to the ethylenic unsaturation of the ethylenically-unsaturated-functional monomer. In the case of the hard crosslinker, the functional groups are bonded via an aliphatic group of up to 10 carbon atoms, to a central moiety that is aromatic in nature, that is, comprises a group that has the rigidity characteristics of a benzene ring. Illustrative of such rigid groups are aromatic rings such as benzene, biphenyl, anthracyl, benzophenone, norbornyl, and the like. Such hard crosslinkers raise the $T_g$ of the cured coating, The soft crosslinker contains the functional groups bonded to a central moiety that is aliphatic in nature, that is, comprises a group that has the flexibility of an alkane or an alkyl benzene containing group. Illustrative of such flexible groups are the residues of ethylene glycol, diethylene glycol, 2,2-bis(4-hydroxyphenyl)propane, 2,2,-bis(4-hydroxyphenyl)fluorinated alkanes, and the like. Such soft crosslinkers toughen the cured coating and can raise the $T_g$ of the cured coating, but not as high as the typical hard crosslinker, Another feature of the primary coating is that it tenaciously bonds to surfaces onto which it is coated as well as securely tie up any inorganic filler that is included in the primary coating formulation. In order to achieve this, the coating contains a coupling agent as part of its formulation. These coupling agents provide chemical bonding to the surface to which the coating is applied. Chemical bonding means strong and weak bonding forces. Strong bonding forces, as used herein, refers to covalent, ionic, hydrogen bonding and complexation, and weak bonding forces, encompasses the other forms of bonding. Where weak bonding forces are employed, the extent of such bonding is such that the adhesion to the surface is of the nature of a stronger bonding force. For example, van der Waal forces are weak bonding forces. In the case of the invention, the amount of such forces existing between the coating and the surface will be sufficient to give the performance of a stronger bonding force.

A desirable coupling agent is a material, such as a molecule, that is functionally complementary to the ethylenically-unsaturated-functional monomer. Desirably, the coupling agent contains a functional group that is reactable with the ethylenic unsaturation. Preferably, the functional group is an acrylic-type ethylenic unsaturation. At another part of the coupling agent molecule is a surface bonding group that can impart one or more properties to the primary coating:

1) chemical bonding capabilities to the substrate surface to which the primary coating is applied; and/or
2) wetting agent properties in that it reduces the surface tension of the coating, causing the coating to spread across or penetrate more easily the surface of the substrate onto which the primary coating is applied.

The utilization the primary coating with fluoride is a special and significant embodiment of the invention. The fluoride component optionally provided in the primary coating is desirably present in the coating such that it is leachable from the coating over an extended period of time.

In order to cure the primary coating, the primary coating formulation is provided with a conventional free-radical catalytic curing agent and/or a free-radical photoinitiator. When both are provided, the coating can be cured by each system, preferably by both to insure that volatile monomeric components are not left as residual components in the coating. This avoids the possibility of toxic reaction to the presence of such volatile monomeric components.

In respect to the above processes, the invention relates to the improvement where the primary coating comprises a two component system of:

(a) a first component comprising:
  (1) the fluoride source, such as a particulate siliceous fluoride containing filler in which the fluoride is water leachable;
  (2) a coupling agent, such as one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds;
  (3) a photoinitiator; if desired, a radiopaguing agent; and, if desired, a buffering agent; and
(b) a second component comprising:
  (1) the ethylenically-unsaturated-functional monomer;
  (2) a soft crosslinker such as 2,2-bis(4-methacryloxy 2-ethoxyphenyl) propane, diethyleneglycol bismethacrylate, and the like;
  (3) a hard crosslinker such as one or more of (i) the adduct of pyromellitic acid dianhydride and 2-hydroxyethyl methacrylate, (ii) the adduct of 3,3',4,4'-benzophenonetetracarboxylic dianhydride and 2-hydroxyethylmethacrylate, (iii) 4-methacryloxyethyltrimellitic anhydride, and (iv) other compounds containing at least one group or moiety capable of free radical polymerization and at least one aromatic ring or moiety containing electron-withdrawing substituents that do not interfere with free radical polymerization;
  (4) a photoinitiator;
  (5) a polymerized carboxylic acid;
  (6) a free-radical scavenger; and
  (7) a curing catalyst.

In another embodiment of the primary coating, it may be a light-curable adhesive composition of the following two-component system:

(a) a first component comprising:
  (1) a fluoride source such as a particulate siliceous fluoride containing filler in which the fluoride is water leachable;
  (2) a soft crosslinker;
  (3) an ethylenically-unsaturated-functional monomer;
  (4) a photoinitiator;
  (5) a free-radical scavenger;
  (6) a thermal initiator;
  7) a polymerized carboxylic acid;
  (8) a hard crosslinker such as one or more of (i) the adduct of pyromellitic acid dianhydride and 2-hydroxyethyl methacrylate; (ii) the adduct of 3,3',4,4'-benzophenonetetracarboxylic dianhydride and 2-hydroxyethylmethacrylate, (iii) 4-methacryloxyethyltrimellitic anhydride, and (iv) other compounds containing at least one group or moiety capable of free radical polymerization and at least one aromatic ring or moiety containing electron-withdrawing substituents that do not interfere with free radical polymerization, and
(b) a second component comprising:
  (1) a fluoride source such as a particulate siliceous fluoride containing filler in which the fluoride is water leachable;
  (2) a soft crosslinker;
  (3) an ethylenically-unsaturated-functional monomer;
  (4) a coupling agent such as one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds;
  (5) a photoinitiator; if desired, a radiopaguing agent; and, if desired, a buffering agent.

A more specific embodiment of the primary coating composition is the following composition:

1. A particulate glass having the composition set forth in Table 1 below;
2. A coupling agent:
  The alkali metal salt of the adduct of N-(p-tolyl)glycine and glycidyl methacrylate; e.g.,

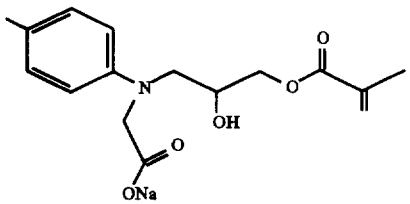

1. A hard crosslinker: The adduct of pyromellitic acid dianhydride and 2-hydroxyethyl methacrylate;
2. A photoinitiator: Ethyl 4-dimethylamino benzoate and camphoquinone (i.e., 2,3-bornanedione);
3. A soft crosslinker: Ethoxylated bisphenol A dimethacrylate and the adduct of glycidylmethacrylate and bisphenol A,
4. An ethylenically-unsaturated-functional monomer: 2-hydroxyethyl methacrylate;
5. Butylated hydroxytoluene free radical scavenger.
6. A polycarboxylic acid;
7. Benzoyl peroxide or other peroxides that cause free radical addition at about 55° C. or at a lower temperature.

The primer coating involves a two part (package) composition, comprising (a) a compound selected from the group consisting of (1) N-phenylglycine, (2) the adduct of N-(p-tolyl) glycine and glycidyl methacrylate, (3) the addition reaction product of N-phenylglycine and glycidyl methacrylate, (4) N(p-tolyl) glycine, N-phenylalanine, sarkosine, N-lauroylsarkosine, glycine, N,N-dimethyl-glycine, 3-(N-phenyl) amino propionic acid, 3-(N-p-tolyl) amino propionic acid, omega-amino fatty acids, N-substituted-omega-amino fatty acids, and the other amino acids; in which each member of the group of (1), (2), (3) and (4) that is present in the solution is an alkali metal salt form of that member, and (b) a composition comprising at least one monomer selected from the group consisting of (1) the addition reaction product of pyromellitic acid dianhydride and 2-hydroxyethyl methacrylate, (2) the addition reaction product of 3,3', 4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization.

The use of the primer coating composition involves, in one preferred embodiment the steps of (a) first contacting the surface with an aqueous solution comprising at least one strong acid or acidic salt in order to condition the surface, (b) then contacting the surface with a solution comprising a solvent and at least one compound selected from the group consisting of (1) N-phenylglycine, (2) the adduct of N-(p-tolyl)glycine and glycidyl methacrylate, (3) the addition reaction product of N-phenylglycine and glycidyl methacrylate, and (4) other amino acids, in which each member of the group of (1), (2), (3) and (4) that is present in the solution is an alkali metal salt form of that member, heat the surface to remove the solvent or maintain the surface at ambient temperature until the solvent is evaporated, and (c) then contacting the surface with a solution comprising at least one monomer selected from the group consisting of (1) the addition reaction product of pyromellitic acid dianhydride and 2-hydroxyethyl methacrylate, (2) the addition reaction product of 3,3', 4,4'-benzophenone tetracarboxylic dianhydride and 2-hydroxyethyl methacrylate, (3) 4-methacryloxyethyltrimellitic-anhydride, and (4) other compounds containing at least one group or moiety capable of free radical polymerization and at least one aromatic ring or moiety containing electron-withdrawing substituents that do not interfere with free radical polymerization (d) heat the surface to remove residual solvent or maintain the surface at ambient temperature until the solvent is evaporated from the primer coating and the coating is fully reacted.

DETAIL DESCRIPTION OF THE INVENTION

Figure 1:
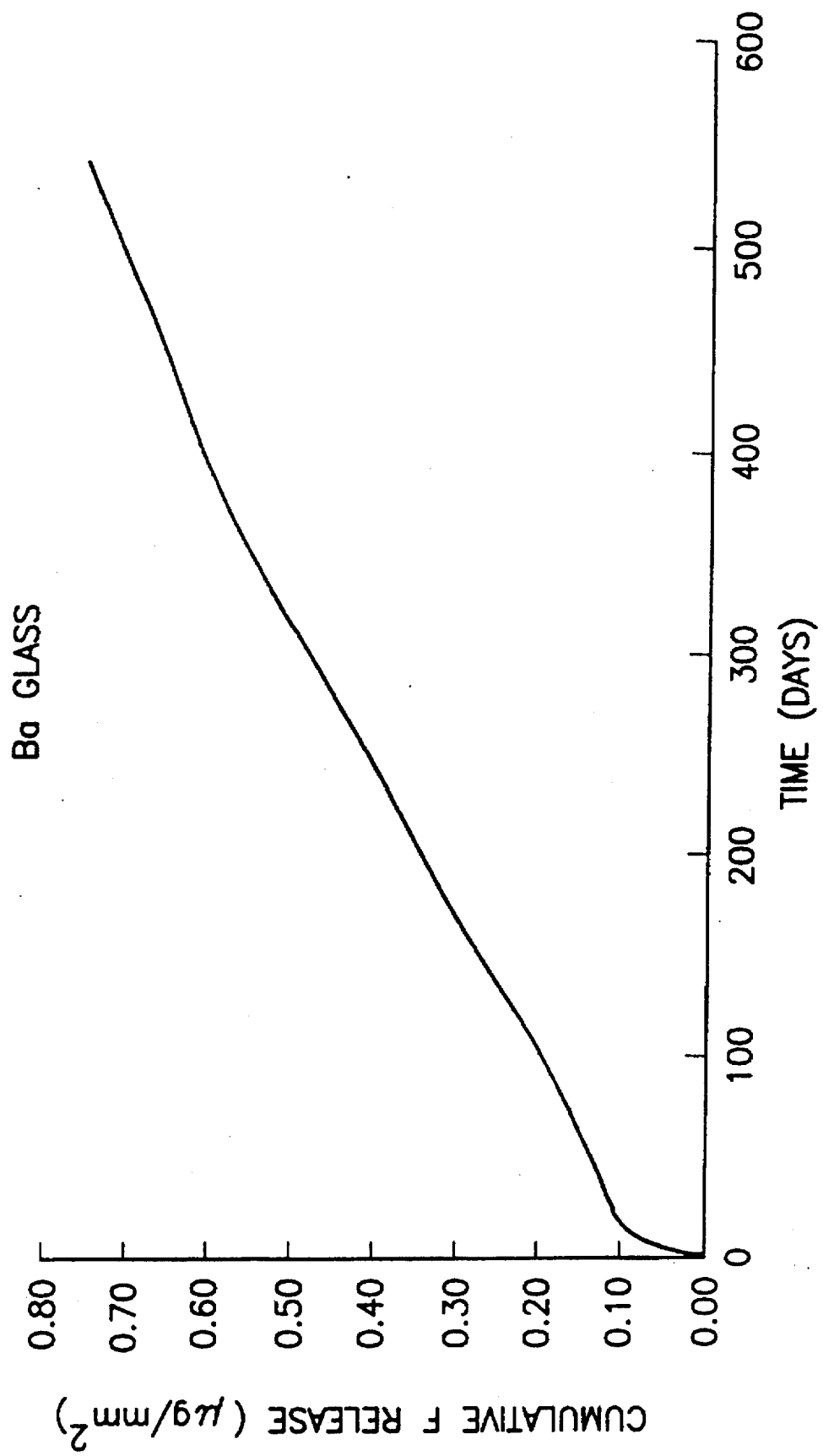
FIG. 1 is a graph showing the uniform, long term leaching of fluoride from a fluoride source used in making a primary coating.

This invention relates to a process for orally implanting a prosthetic that serves to support and reinforce either another prosthetic or teeth. The invention is directed to the surgical dental implant process within the alveolar bone where the improvement involves implanting a metal prothesis that has an outer coat of the primary coating. The invention includes all of the steps conventionally practiced in dental implantation plus the step or steps of coating one or more of the prosthesis used in such implantation with the primary coating. In addition, the invention also relates to the steps in which a prosthesis is imbedded in the alveolar bone, and the bone contiguous to the prosthesis is infused by application of the primary coating. In addition, the invention further relates to the steps in which a second prosthesis is bonded to the prosthesis imbedded in bone, in which the interface between the two prosthesis contains a layer of the primary coating serving to interbond the two prosthesis.

The Primary Coating

The primary coating is typically a crosslinked heat and/or light set resin that contains hygroscopic groups that attract water to the coating. When the crosslinking is not too extensive, the primary coating can absorb enough water that it can swell. The amount of water that the primary coating can absorb can be as high as 37 weight percent. The backbone of the polymer providing the hygroscopic groups of the resin phase of the primary coating is typically aliphatic and may contain groups therein that enhance the hydrophillicity of the resin phase. Though the primary coating's resin can be made by a condensation reaction, such as by low temperature resin formation by the reaction of a blocked polyisocyanate with a polyol, the resin is typically the in situ reaction product of one or more of a polymerizable ethylenically unsaturated organic monomer containing groups that are attractive to water. Thus the components of the primary coating may be (a) an ethylenically unsaturated-functional monomer that contains a hygroscopic group. Typical of such groups are hydroxyl, amide, amine, aliphatic ether, amine, hydroxyalkyl amine, hydroxyalkyl amide, pyrrolidone, ureyl, and the like. Illustrative of such monomers are the following:

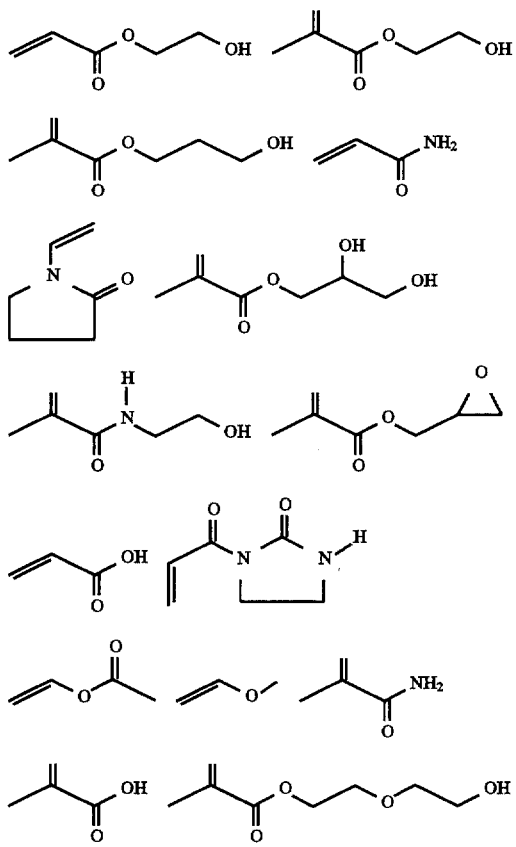

A particularly desirable ethylenically unsaturated-functional monomer is an acrylic-type monomer having the following structure:

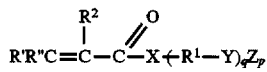

wherein R' and R", individually, are hydrogen, alkyl of 1 to about 4 carbon atoms, monocyclic aryl, such as phenyl, alkyl phenyl where the arkyl is 1 to about 3 carbon atoms, cyclohexyl, and the like; $R^2$ is hydrogen, alkyl of 1 to about 3 carbon atoms, and the like; X is O, S and N—$R^3$, where $R^3$ is hydrogen, alkyl of 1 to about 4 carbon atoms, —$R^1$—Y, and the like; $R^1$ is a divalent radical connecting Y to X, and may be one of the following:

—$CH_2CH_2CH_2$—

OH

—$CH_2CHCH_2$—

—$CH_2CHR^4OCH_2CHR^4$— wherein each $R^4$ is hydrogen or alkyl of 1 to about 3 carbon atoms; and Y is OH, $NR^5$, SH, $OR^6$, where $R^5$ is hydrogen, methylol, methylol methyl ether, $R^6$ is alkyl of 1 to about 3 carbon atoms provided that $R^1$ is —$CH_2$—, and the like; q is 0 or 1 and p is 0 or 1, and p is 0 when q is 1 and 1 when q is 0; Z is hydrogen.

A particularly desirable thermosetting coating is based on 2-hydroxyethyl methylmethacrylate ("HEMA"), 2-hydroxyethyl acrylate, 2,3-dihydroxypropyl methacrylate, acrylamide, methacrylamide, hydroxyalkyl acrylamide, hydroxyalkyl methacrylamide, and the like materials.

(b) A linear polycarboxylic acid or acid salt that contains a plurality of pendant carboxyl or carboxylic acid salt groups such as one having the formula:

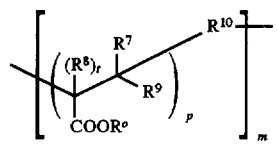

$R^o$ is hydrogen or alkali metal, such as Li, Na, K, Ru and Cs to form a salt, and preferably hydrogen, sodium or potassium, $R^7$ and $R^8$ are hydrogen or alkyl containing from 1 to about 3 carbon atoms, $R^9$ is hydrogen, alkyl of 1 to about 3 carbon atoms, or $COOR^o$, provided that $R^9$ is not alkyl when $R^7$ is alkyl, $R^{10}$ is a valence bond when the formula is for a homopolymer or a divalent organic moiety of a polymerized ethylenically unsaturated monomer, p is a number representing at least 40 mole percent of the units of the polymer, and m is a number providing for a molecular weight of from about 2,000 to about 500,000. Particularly preferred polycarboxylic acids are polyacrylic acid, polymaleic acid, polyitaconic acid, or a copolymer of acrylic acid, maleic acid, fumaric acid or itaconic acid with other ethylenically unsaturated monomers such as methyl acrylate, ethylacrylate, methylmethacrylate, vinyl acetate, vinylmethylether, styrene, α-methylstyrene, vinylcyclohexane, dimethylfumarate, ethylene, and the like. Preferably, these polymers have molecular weights $M_w$ of about 3000–250,000. In one embodiment, the polycarboxylic acid or the salt form may contain about 1–5 weight % of d-tartaric acids.]

(c) A desirable coupling agent is an acrylic-type monomer that possesses acrylic-type unsaturation and contains a surface bonding group possessing one or more of the following groups:

| | |
|---|---|
| i) an alkylene polyether; | vi) tertiary amine |
| ii) hydroxyl | vii) phosphoryl |
| iii) carboxyl | viii) phosphinyl |
| iv) carboxylic acid salt | ix) stannoyl |
| v) quaternary ammonium | x) amide |
| | xi) alkylene amine |

A preferred coupling agent is a simple aromatic substituted amino acid or its alkali metal salt such as the free acid or alkali metal salt of (i) N-phenylglycine, (ii) the adduct of N-(p-tolyl)glycine and glycidyl methacrylate, which are illustrated by the structures:

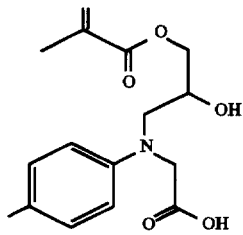

and

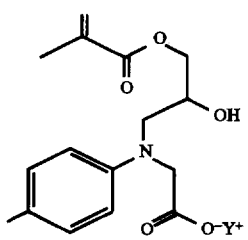

where Y is one of the alkali metals, i.e., lithium, sodium, potassium, rubidium and cesium, preferably sodium or potassium, and (iii) the adduct of N-phenylglycine and glycidyl methacrylate, the alkali metal salt thereof, or the mixture of the foregoing two compounds, which compounds are illustrated by the structures, and (iii) the adduct of N-phenylglycine and glycidyl methacrylate, which are illustrated by the structures:

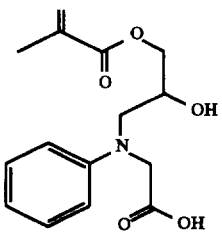

-continued and

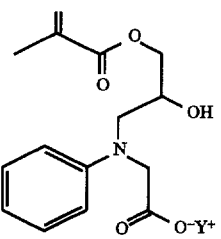

where Y is described above; or the mixture of the foregoing two compounds, alone or in combination with a compound containing at least one group or moiety capable of free radical polymerization and at least one aromatic ring or moiety containing one or more electron-withdrawing substituent that does not interfere with free radical polymerization.

The purpose of the coupling agent is to interreact with the polymerization of the aforementioned ethylenically unsaturated-functional monomer that contains a hygroscopic group and enhance wetting by the resulting resin of proteinaceous surfaces by the surfaces interaction with the carboxylic acid or carboxylic acid salt group in the bonding agent.

(d) A number of acrylic coating resins rely on polyacrylyl substituted monomers to crosslink and chain extend the polymer that comes into existence on polymerization in the presence of an polymerization initiator. For example, the pure forms of HEMA typically contain small amounts of ethylene glycol dimethacrylate which will crosslink a polymer based on HEMA. The degree of crosslink may be so minuscule as to have little effect on the ultimate properties of the polymer. Crosslinking agents are frequently added to HEMA based resins to impart a particular quality of crosslinking and toughness to the cured resin. For example, diethylene glycol dimethacrylate can otherwise lower the crosslink density of the resin which may impart toughness to the resulting cured polymer. Those types of crosslinkers would be considered a soft crosslinker, as defined above. However, in the practice of this invention, it is desired to use dual crosslinkers, one that is hard and one that is soft. In this respect, one may include the above crosslinker, in its normal impurity concentrations, as part of the soft crosslinker, but in the preferred embodiment, it is desirable to employ hard and soft crosslinkers that contain at least two acrylyl groups bonded to aromatic containing moiety(ies). A desirable hard crosslinker is characterized by the following formulae:

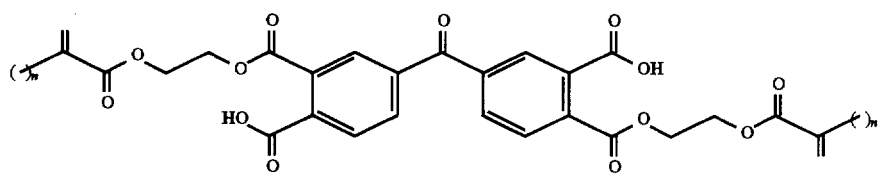

"A"

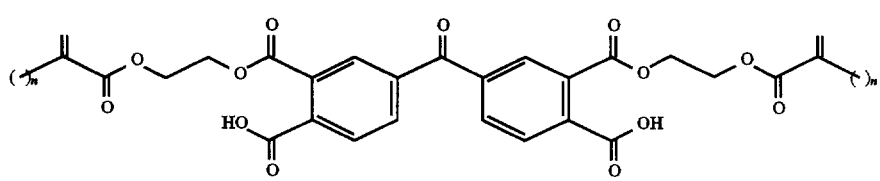

-continued
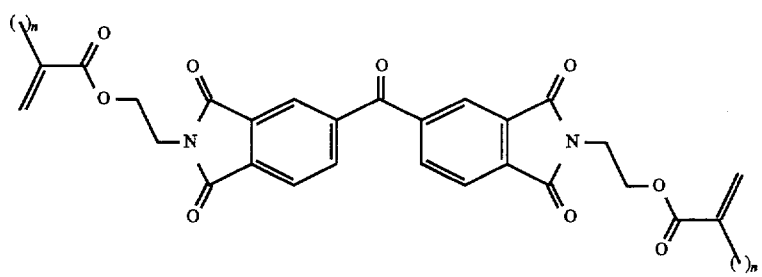
"B"
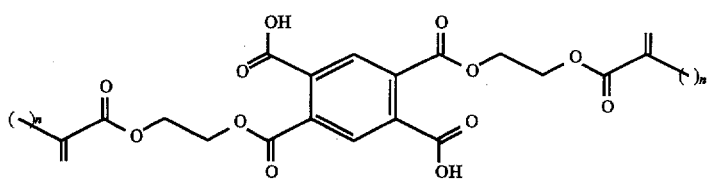
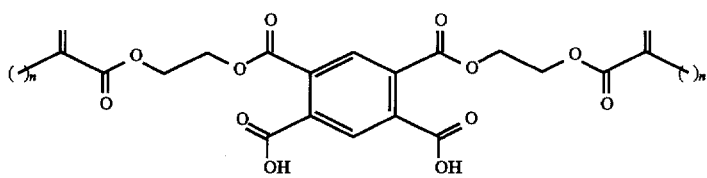
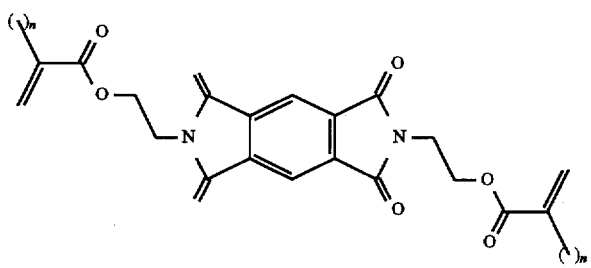
"C"
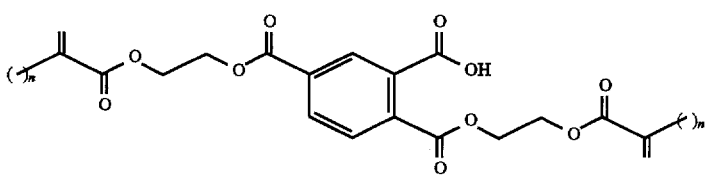
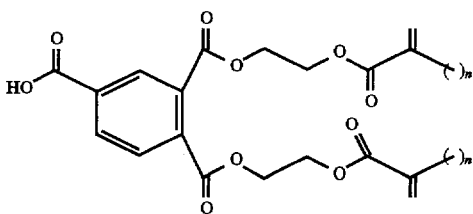
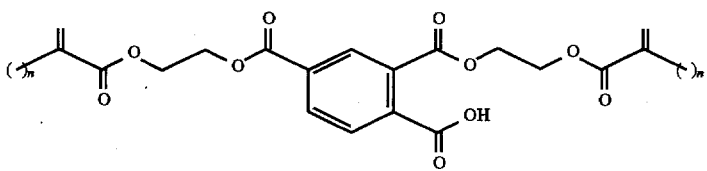

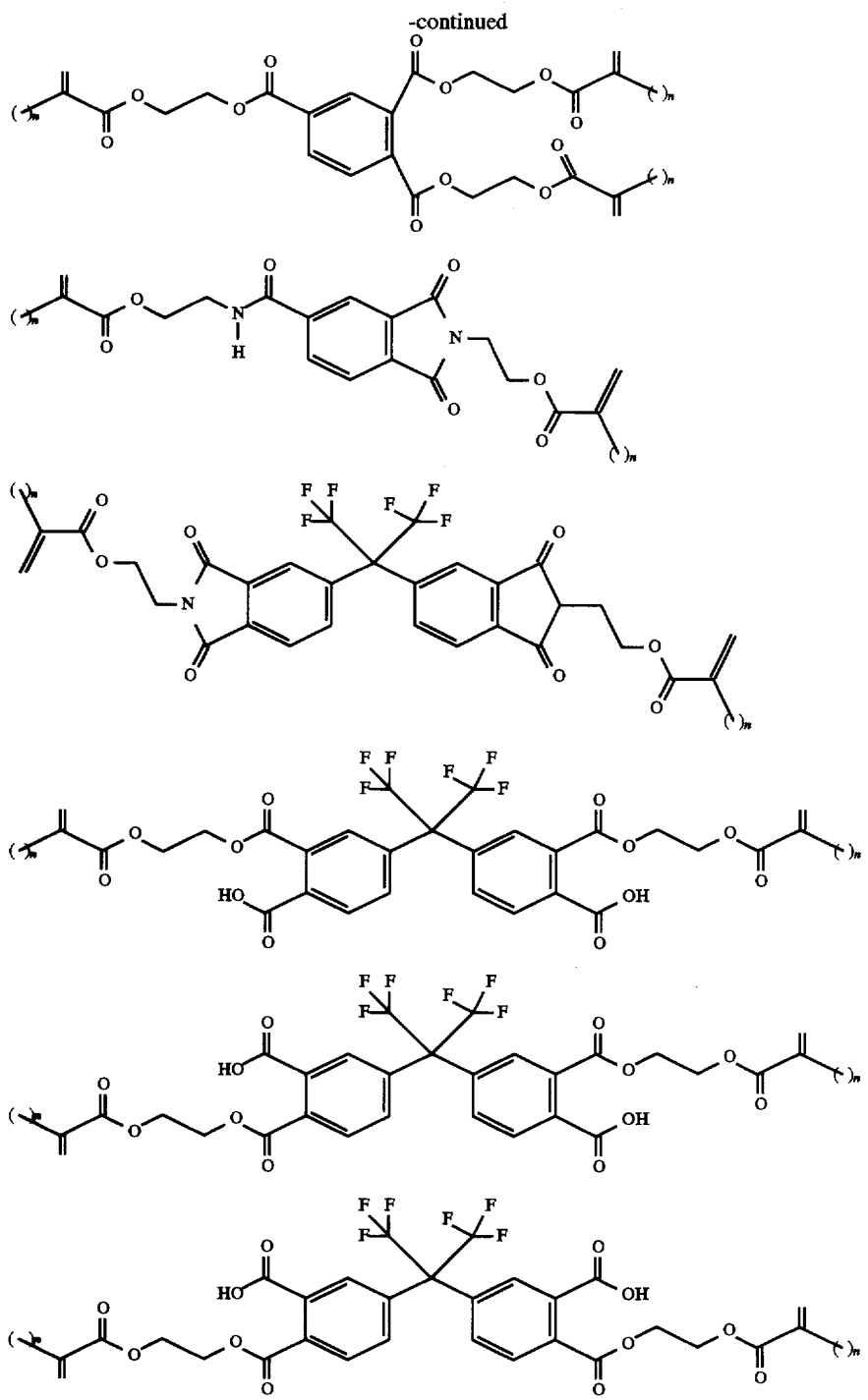

"D"

wherein n is 0 or 1. The preferred hard crosslinking agent is one of (i) the esters or imides of pyromellitic acid dianhydride and 2-hydroxyethyl methacrylate or 2-aminoethyl methacrylate, or the corresponding acrylates, as illustrated in group B above, (ii) the ester or imides of 3,3',4,4'-benzophenonetetracarboxylic dianhydride and 2-hydroxyethylmethacrylate or 2-aminoethyl methacrylate, or the corresponding acrylates, as illustrated in group A above, (iii) the esters and imide/amides of 4-trimellitic acid anhydride and 2-hydroxyethylmethacrylate or 2-aminoethyl methacrylate, or the corresponding acrylates, as illustrated in group C above, (iv) the ester or imides of 2,2-bis(3,4,-dianhydridophenyl)-1,1,1,3,3,3-hexafluoropropane and 2-hydroxyethyl methacrylate or 2-aminoethyl methacrylate, or the corresponding acrylates, as illustrated in group D above, and (iv) other compounds containing at least one group or moiety capable of free radical polymerization and at least one aromatic ring or moiety containing electron-withdrawing substituents that do not interfere with free radical polymerization. The soft crosslinker is typically an diacrylic or dimethacrylic ester or ether of bisphenol A, but also include as soft crosslinkers are the other glycol dimethacrylates and diacrylates mentioned herein. Preferred soft crosslinkers are ethoxylated bisphenol A dimethacrylate and the adduct of glycidylmethacrylate and bisphenol A, (e) The fluoride component is present in the primary coating as a component of a non-resinous component of the formulation. The fluoride component may be, but need not be soluble in the resin component of the primary coating. In the preferred practice of the invention, the fluoride component in the primary coating will dissolve in water and to the extent the water is removed from the fluoride source, fluoride is carried with it. As noted above, the particularly desirable form of the fluoride component, is an inorganic fluoride in which the fluoride is present, e.g., in the form of an fluorosilicate structure or an alumina fluoride structure. The fluoride source of the patent is a glass composition in which the fluoride content is derived from an alkaline earth metal fluoride such as calcium fluoride, barium fluoride and strontium fluoride. A most preferred fluoride source is described in U.S. Pat. No. 5,360,770 which is incorporated herein by reference, particularly the examples and illustration of the patent that show how to make the fluoride source. As noted above, the primary coating is optionally provided with a leachable fluoride component. The fluoride is leachable from the coating over a three to four month period. This means that after many days and even months, the coating should be able to release small measured amounts of fluoride into the wound area. The longevity of the fluoride in the coating and the ability to meter it from the coating are dependent on a number of factors, such as:

the concentration of fluoride in the coating;

the nature of the chemical bond of the fluoride within the coating composition;

the level of hygroscopicity of the coating;

if the fluoride is part of a solid, the degree of particulateness of the solid, coupled with the rate at which fluoride can be leached from the solid;

if the fluoride is part of a liquid molecule, the rate at which the fluoride is cleaved from the molecule to form a leachable fluoride; and if the fluoride is part of a polymer, the rate at which fluoride in the polymer can be solubilized and leached from the polymer.

A particularly desirable form of the fluoride component, is an inorganic fluoride in which the fluoride is present, e.g., in the form of an fluorosilicate structure or an alumina fluoride structure. Illustrative of such fluoride structures are fluorite (or fluorspar), $CaF_2$, $BaF_2$, $SrF_2$, cryolite, $Na_3AlF_6$, and fluorapatite, $3Ca_3(PO_4)_2Ca(F,Cl)_2$. A preferred fluoride source is described in U.S. Pat. No. 5,360,770. The fluoride source of the patent is a glass composition in which the fluoride content is derived from an alkaline earth metal fluoride such as calcium fluoride, barium fluoride and strontium fluoride. A particularly preferred glass composition that provides fluoride is the following:

TABLE 1

Figure 2:
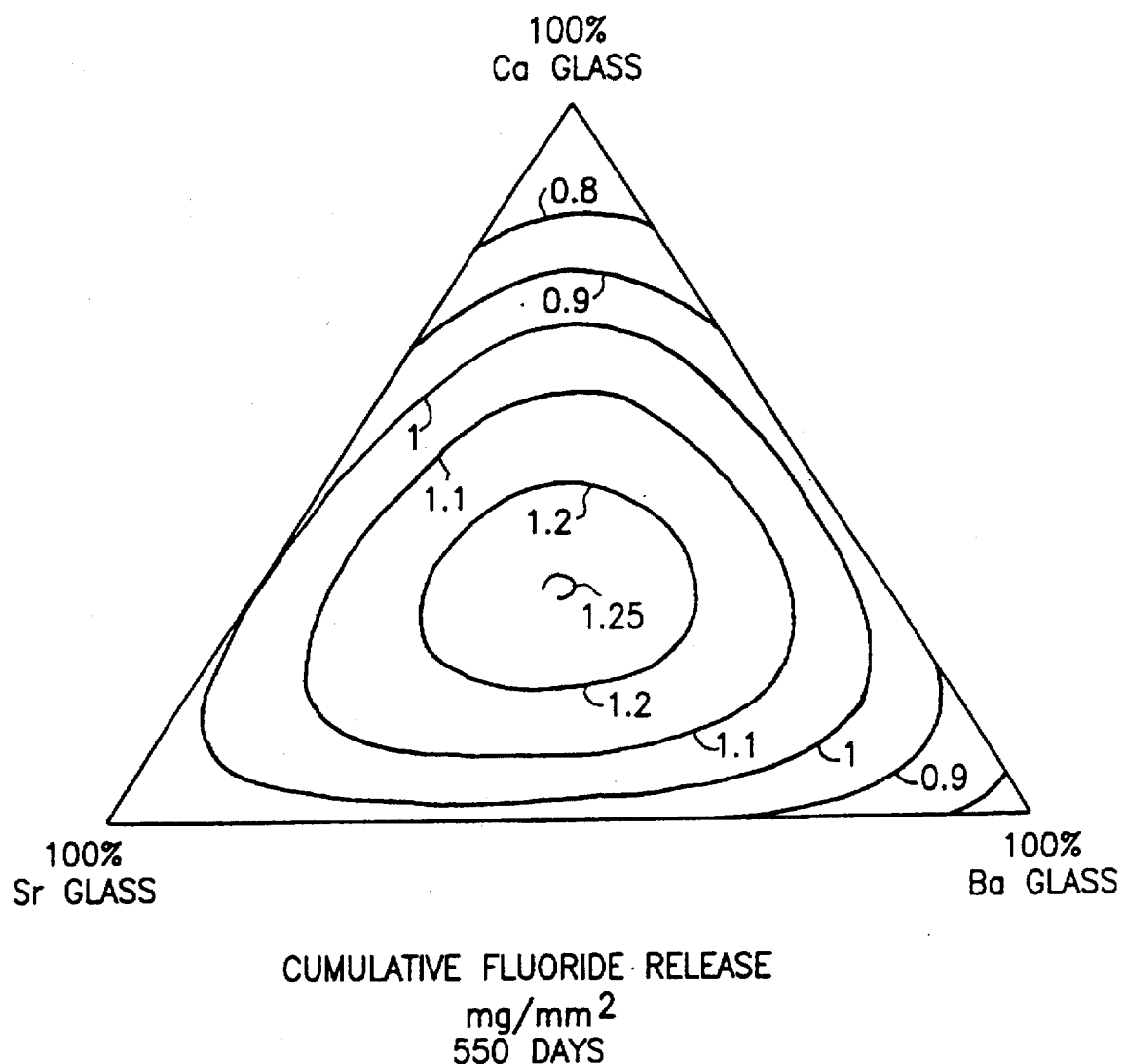
FIG. 2 is an area plot of concentration of a siliceous fluoride source from which one may obtain long term and uniform leaching of fluoride.

| Component | Mole % | Component | Mole % |
| --- | --- | --- | --- |
| $SiO_2$ | 17.6–21.6 | $P_2O_5$ | 0.8–3.5 |
| $Al_2O_3$ | 9.0–11.0 | $Na_2O$ | 0.5–3.0 |
| MO | 7.9–19.7 | F | 42.2–56.1 | in which M is an alkaline earth metal and MO is barium oxide and barium oxide binary and ternary mixtures with other alkaline earth metal oxides, such as BaO, BaO—CaO, BaO—SrO and CaO—BaO—SrO. Such preferred source of fluoride not only provides long term fluoride release from the primary coating but it also provides an essentially uniform release of fluoride over that period of time. FIGS. 1 and 2 illustrate the long term fluoride leachability of this fluoride source. FIG. 1 illustrates the release of fluoride by placing the aforementioned barium oxide based glass in water and determining the release of fluoride over an extended period of time. As can be seen, the fluoride release follows a straight line showing uniform release over 550 days, about 1½ years. FIG. 2 shows area plots of ingredients in order to optimize the glass formulation for maximizing the fluoride release over an extended period, e.g., 1½ years.

(f) Also included in the formulation, as an optional ingredient, is a photoinitiator. According to one aspect this invention, the light-initiated curing of a polymerizable matrix material involves photosensitization of light-sensitive compounds by ultraviolet or visible light, which, in turn, initiates polymerization of the matrix material. The photoinitiator to be used in this invention comprises a combination of a photosensitive ketone and a tertiary amine. Typical photosensitive ketones include benzophenone, acetophenone, thioxanthen-9-one, 9-fluorenone, anthraquinone, 4'-methoxyacetophenone, diethoxyacetophenone, biacetyl, 2,3-pentadione, benzyl, 4,4'-methoxybenzil, 4,4'-oxidibenzil, and 2,3-bornadione (dl camphroquinone). Typical tertiary amines include ethyl-4-dimethyl amino benzoate, ethyl-2-dimethyl amino benzoate, 4,4'-bis(dimethylamino) benzophenone, N-methyldiethanolamine, and dimethylaminobenzaldehyde. A preferred combination of the photoinitiators is 2,3-bornanedione with ethyl-4-dimethyl amino benzoate. Other suitable initiator are illustrated in U.S. Pat. No. 4,674,980 to Ibsen, et al., the disclosure of which is incorporated by reference. Alternatively, any known photosensitizing system which can function effectively in a paste/paste composition when exposed to light may substitute for the above-named compounds or combinations. The amount of the photoinitiator should be sufficient to initiate polymerization in a selected resin and complete it in depth within about half a minute when the filler-resin composition is exposed to a visible-light output of at least 5,000 foot candles. In addition, any known free-radical scavenger (anti-oxidants) such as butylated hydroxytoluene can be used to scavenge small amounts of free radicals generated during extended shelf storage.

(g) The polymerization system of the primary coating composition may depend on effecting cure with either the photoinitiator or by use of a thermal initiator, which is a typical thermal curing agent known in the art. Illustrative of these are benzoyl peroxide, dicumyl peroxide, ditertiary butyl peroxide, tertiary butyl hydroperoxide, cumyl hydroperoxide, or other suitable peroxides may initiate polymerization of the polymerizable ethylenically unsaturated components of the primary coating. Addition of such thermal initiators is desirable to insure complete polymerization. Even when light alone does not cure the matrix material, the peroxide initiates curing of the uncured material thermally upon standing. Benzoyl peroxide may be used together with 2-hydroxyethyl-p-toluidine.

The primary coating may contain pigments such as iron oxide or titanium oxide and a color stabilizing agent such as 2,2-hydroxy-5-tert. octyl phenylbenzotriazole.

In formulating the primary coating, the selection of the ingredients in formulating the coating is narrowly critical.

Illustrative of such a formulation is the paste/paste primary coating composition as set forth in Table 2.

TABLE 2

| Ingredients | Percentage by Weight |
|---|---|
| Paste A | |
| Glass, fluoride source | 0–85 |
| Ethylenically unsaturated monomer, e.g., 2-hydroxyethyl methacrylate | 3–40 |
| Soft Crosslinker, e.g., Ethoxylated bisphenol A dimethacrylate | 10–60 |
| 2,3-bornanedione | 0.03–0.30 |
| Butylated hydroxytoluene | 0.001–1.0 |
| Benzoyl peroxide | 0.005–0.10 |
| Polycarboxylic acid, eg., polyacrylic acid | 0–8 |
| Hard Crosslinker, e.g., PMDM | 2–20 |
| d-Tartaric acid | 0–1 |
| 2,2-Hydroxy-5-tert-octyl phenylbenzotriazole | 0.00–2 |
| Ethyl 4-dimethylaminobenzoate | 0.00–2 |
| Paste B | |
| Glass, fluoride source | 0–70 |
| Ethylenically unsaturated monomer, e.g., 2-hydroxyethyl methacrylate | 0–45 |
| Soft Crosslinker, e.g., ethoxylated bisphenol A dimethacrylate | 10–90 |
| Coupling agent, e.g., Na NTG-GMA, NGT-GMA | 1–20 |
| Zinc oxide | 0–15 |
| Barium tungstate | 0–15 |
| Ethyl 4-dimethylamino benzoate | 0–2.0 |
| 2,3-bornanedione | 0.05–0.30 |
| Butylated hydroxytoluene | 0.005–0.10 |
| Titanium dioxide | 0.0–3.0 |
| 2,2-Hydroxy-5-tert-octyl phenylbenztriazole | 0.00–2 |

The two pastes, Paste A and Paste B, are preferably mixed well in equal amounts. The pastes may be mixed with a spatula or put onto a blade mixer prior to application to a surface. For example, the physician or technician may use the system by combining the pastes in the ratios desired, and then mixing them. The resulting paste is then applied to the surface as needed. The coating will self-cure in about 20–30 minutes, but cures instantly on exposure to light. Light having a wave length of about 480 ηM at an intensity of about 5000 foot-candles is preferred. An exposure of about 30 second is sufficient to cure the cement in most applications.

As noted above, a primer coating may be applied to the treated surface before coating on the primary coating. This may be effected by the following procedure:

(1) First contacting the surface with an aqueous solution comprising at least one strong acid or acidic salt with a dispensable brush or a skube (a preformed Styrofoam™ sponge) in order to condition the surface. Leave for 15 seconds and blot dry with a skube. Note: if hemorrhage is in the area, use a hemostatic solution or the aqueous solution with a hemostatic solution to control seepage and keep the bonding surface dry.

(2) Immediately mix with stirring with a dispensable brush a solution comprising a solvent and at least one compound selected from the group consisting of (1) N-phenylglycine, (2) the adduct of N-(p-tolyl)glycine and glycidyl methacrylate, (3) the addition reaction product of N-phenylglycine and glycidyl methacrylate, and (4) other amino acids, in which each member of the group of (1), (2), (3) and (4) that is present in the solution is an alkali metal salt form of that member, and a solution comprising at least one monomer selected from the group consisting of (1) the addition reaction product of pyromellitic acid dianhydride and 2-hydroxyethyl methacrylate, (2) the addition reaction product of 3,3', 4,4'-benzophenone tetracarboxylic dianhydride and 2-hydroxyethyl methacrylate, (3) 4-methacryloxyethyltrimellitic-anhydride, and (4) other compounds containing at least one group or moiety capable of free radical polymerization and at least one aromatic ring or moiety containing electron-withdrawing substituents that do not interfere with free radical polymerization. Apply 3–5 coats of the mixture onto the prepared bonding surface with the dispensable brush used for mixing. Allow to dry for 15 seconds.

(3) Mix Paste A and B together and load into a syringe. Immediately inject the paste mixture onto the prepared bonding surface and light-activate for 30 seconds. This will effect cure.

The above procedure can be effected without using the primer coating. In such an embodiment, it is important to clean the surface to which the primary coating is being applied. Water washing the surface if an acid wash is not recommended or needed will prepare the surface provided the surface is thoroughly dry before applying the primary coating.

As noted above, the invention can invoke forming a cured patch of the primary coating on glass or Teflon® with a knife coater. The coating should be as thin as workable, such as from about 1 to about 100 mils. The patch may have a thickness of about 0.75 mil to about 95 mils, preferably from about 2 to about 50 mils. Its length and width is dependent upon where the patch is to be employed. For example, the patch can be inserted into the bone cavity, typically at the floor of the cavity, that is created for the implant and with paste of the primary coating applied to it, the patch can be adhesively bonded to the bone or prosthesis depending on where the paste is applied. Because the patch is biocompatible, it is not rejected and, as such, will aid the natural growth of new bone without infection. This is particularly the case where the patch contains fluoride.

The primer coating may contain solvent solutions of the free acid or alkali metal salt of (i) N-phenylglycine, (ii) the adduct of N-(p-tolyl)glycine and glycidyl methacrylate, which are illustrated by the structures:

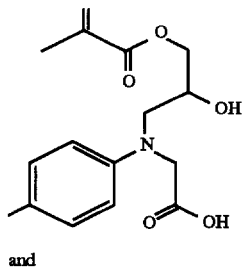

and

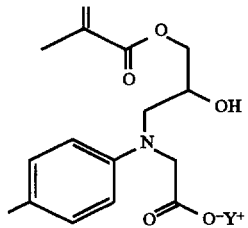

where Y is one of the alkali metals, i.e., lithium, sodium, potassium, rubidium and cesium, preferably sodium or potassium, and (iii) the adduct of N-phenylglycine and glycidyl methacrylate, the alkali metal salt thereof, or the mixture of the foregoing two compounds, which compounds are illustrated by the structures, and (iii) the adduct of N-phenylglycine and glycidyl methacrylate, which are illustrated by the structures:

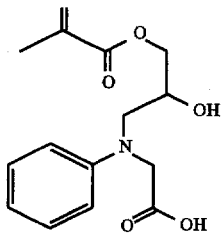

and

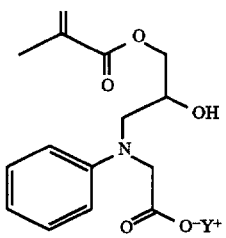

where Y is described above; and the solvent solution of PMDM (see the isomeric mixture of "B" above that describes the adduct of pyromellitic acid dianhydride and 2-hydroxyethyl methacrylate). The preferred solvent is a mixture of water and a polar solvent such as acetone.

When applying the primer coating, the surface may be prepared with an acid wash as disclosed in the aforementioned reissue application. The first stage of the primer coating may be a solvent solution of the NTG-GMA adduct, typically dried before the second solution is applied to it. The second stage is a solution of, e.g., PMDM that is coated over the first stage. That coating is also dried before applying the primary coating. On drying, the primer coating is cured. Drying may be effected at ambient conditions, or accelerated by the addition of heat to the undried coating.

In those cases, the primary coating may be brushed or injected with a conventional hypodermic needle from a conventional hypodermic syringe onto and within the cavity formed by drilling into the alveolar bone. The prosthesis can then be inserted into the cavity by screwing or tapping it in, or if the cavity is oversized for the prosthesis, then the adhesive, with or without a patch, can be used to fill the space between the prosthesis and the bone wall(s) of the cavity. The primary coating can be set by exposing the coating to light or by heating the area to a temperature that causes the initiator to decompose and initiate polymerization, resulting in a cured resin. Bone growth then occurs through and about the cavity to which the primary coating is applied without rejection of the coating. Portions of the prosthesis may not be confined by bone, and may extend through the mucoperiosteum and the gingiva. Those portions may also be coated with the primary coating with or without fluoride. In those instances where the primary coating, with or without fluoride, is applied to bone, it will be desirable to first coat the bone with the primer coating, drying and curing that coating and then applying the primary coating over the cured primer coat. After the primary coat is applied, the prosthetic device may then be implanted so as to contact the uncured primary coat. At this point, the primary coat may be cured resulting in a strong bond to the prosthetic device and the bone surface.

Figure 3:
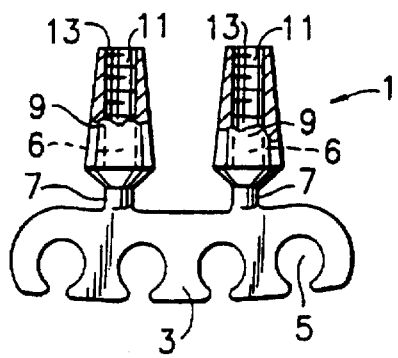
FIG. 3 is side view with partial cross sections of a blade prosthetic implant.
Figure 4:
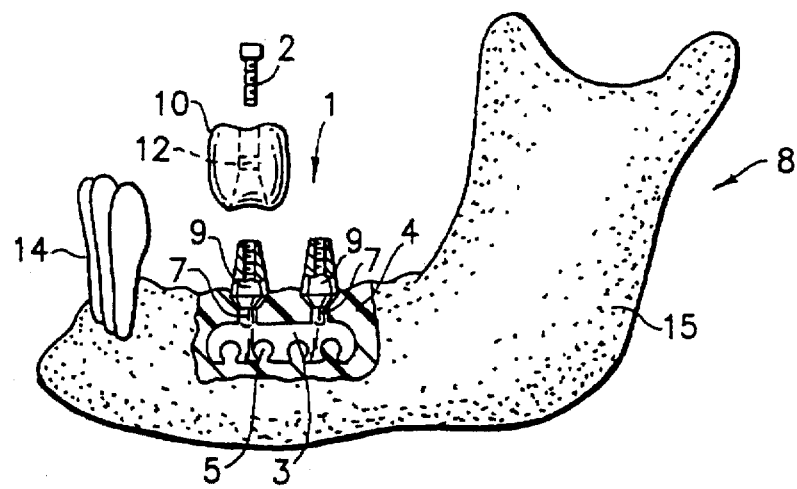
FIG. 4 is a partial cross sectional side view of a mandible in which a blade prosthetic implant is imbedded in the body of the mandible.

FIG. 3 is side view of a blade prosthetic implant 1. In its typical embodiment, it is made wholly of a metal such as stainless steel and its alloys or of titanium and titanium alloys. It comprises blade 3 containing cavities 5 into which bone growth can occur. Attached to blade 3, as shown, are cylindrical pins 7 to which are affixed tapered cylindrical posts or abutment 9. Each post or abutment 9 contains an untapered cylindrical hollow interior 6 that contains helical or advancing spiral thread 11. Interior 6 can be entered through opening 13. FIG. 4 shows implant 8 comprising mandible 15, teeth 14, blade prosthetic implant 1, prosthetic tooth 10 and locking screw 2. In this embodiment, the mandible is drilled to create cavity 4 into which blade prosthetic implant 1 is fitted. Cavity 4 is then filled by injection with primary coating, in this case functioning as a potting material, and on cure of the primary coating, implant 1 is securely bonded in place. If desired, a patch of primary coating can be placed on the bottom of cavity 4, and affixed thereat by the paste of primary coating coating on its surface that directly contacts bone. On the other hand, cavity 4 can be drilled just wide enough to insert blade 3 within cavity 4, and though primary coating may be injected into that space, bone growth can be relied on to fix blade 3 and implant 1 in the bone. Prosthetic tooth 10 is placed over post or abutment 9. The tooth may be made of an acrylic resin or of a conventional composite material. Tooth 10 is screwed to post or abutment 9 with screw 2 typically containing a hex key head.

Figure 5:
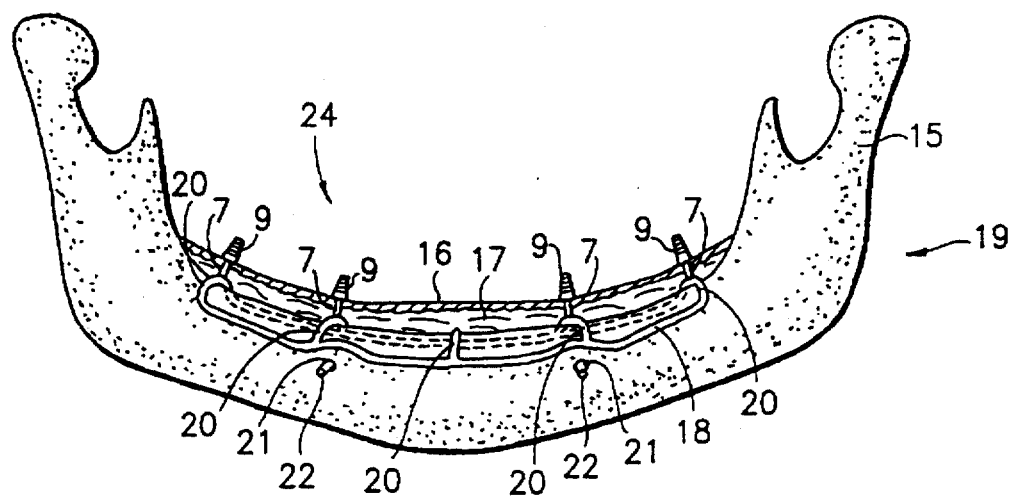
FIG. 5 is a partial cross sectional front view of a mandible containing a sub-periosteal implant.

FIG. 5, a partial cross sectional front view, illustrates subperiosteal implant 19 in which the mandible 15 onto which the implant is made, is shown in cross section. In this subperiosteal implant, implant 24 conforms to the bone surface 15, via wire 18 and crossover braces 20 attached to a similarly positioned wire (not shown) on the other side of the mandible. The oppositely positioned wire (not shown) contains inwardly position pins 22 that are positioned in drilled holes 21. Implant 24 is covered with mucoperiosteum 17, and has posts or abutments 9 extending from pins 7 bonded to braces 20, to be exposed in the mouth above gingiva 16. Bridges, dentures, etc. may be fixed to posts or abutments 9, e.g., as shown in FIGS. 3 and 4.

Figure 6:
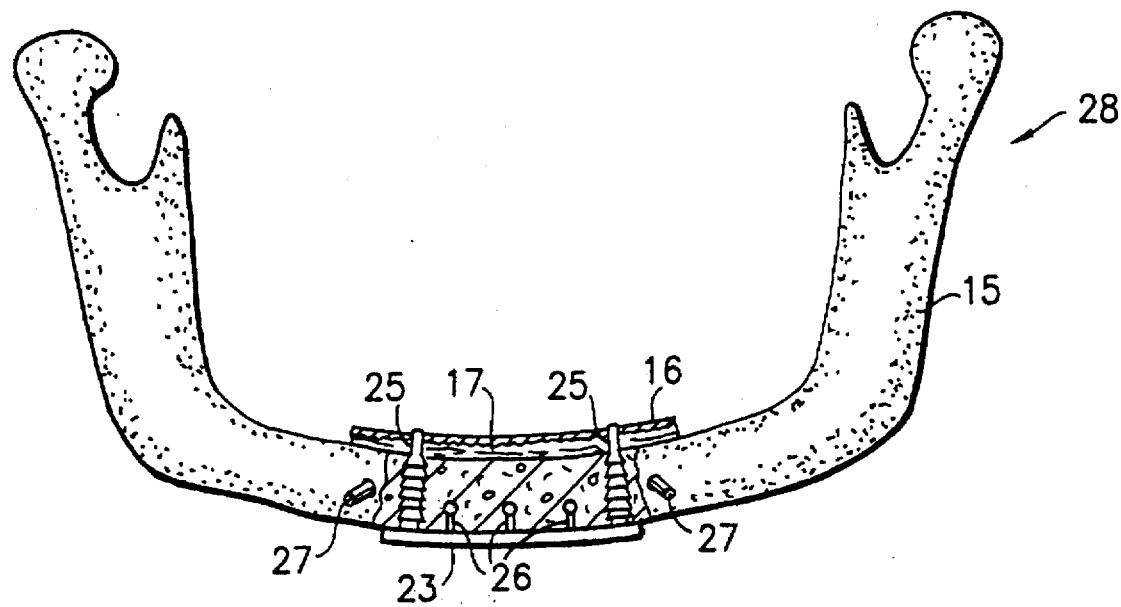
FIG. 6 is a partial cross sectional front view of a mandible containing a trans mandibular implant.
Figure 7:
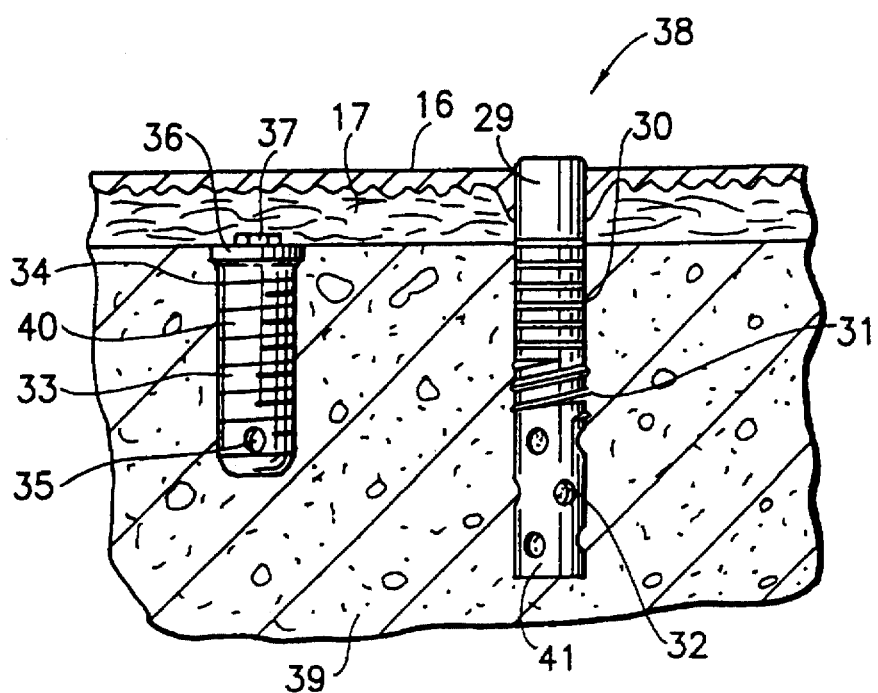
FIG. 7 illustrates a cross sectional side view of a two stage endosseous implant located in alveolar bone.

FIG. 6 is a partial cross sectional front view of a mandible containing a trans-mandibular implant. In this implant, a base surface 23 is placed on the underside of mandible 15, and held in position by pins 26 imbedded in mandible 15. Posts 25 are screwed through base surface 23 and mandible 15 to leave exposed pin extending through mucoperiosteum 17, to be exposed in the mouth above gingival 16. A portion of base surface (not shown) wraps around mandible 15, and is connected to pins 27 inserted into holes drilled in the bone. The FIG. 7 illustrates a cross sectional side view of a two stage endosseous implants located in alveolar bone. In the case of implant 40, it comprising a cylindrical liner containing an exterior thread 34 and a hollow threaded 33 interior into which screw 37 can be placed. Its upper surface 36 lays at the bone 39 surface that interfaces with mucoperiosteum 17. It is provided with a transverse hole into which bone growth will penetrate serving to lock the implant in position. Implant 41 is more elongated and extends through mucoperiosteum 17 and gingiva 16. It comprises an abutment 29, threaded portion 30 and helical threaded portion 31. It also contains a plurality of transverse holes 32 serving to accept bone growth. It interior is hollow and threaded so that a screw can be inserted to hold another prosthetic device, such as a bridge, acrylic tooth, and the like.

The process is practiced by employing conventional surgical implantation techniques. Incisions in the gingiva are required to expose the bone area and reveal the damaged tooth or teeth. Extraction of the damaged tooth is required where tooth repair is not feasible. Exposure of the bone is required for treating the area for reception of the implants. Closure of the gingival flap after installation of the implant is effected by conventional procedures well known in the art.

Test were run to determine bond strengths to substrates involving implants that include bone tissue. Four substrates were tested for bond strengths. They were bovine bone tissue,
   dentin,
   stainless steel,
   enamel,
   porcelain,
   nonprecious (NP) metals
   titanium and
   hydroxyapatite (the principal bone salt, $Ca_5(PO_4)_3OH$, which provides the compressional strength of vertebrate bone).

The metal surfaces were prepared by roughening the surface with a dental burr and then treated with a degreasing agent. The hydroxyapatite surface was etched with 37% phosphoric acid. The bone tissue was treated with a dehydrating agent. The bonding tests[1] were conducted by placing the primary coating (or the primer coating where specifically indicated) on the treated substrate, and cured by exposure to light. A heavy body composite, Marathon™ (sold by Den-Mat, Inc.) was placed in a 5.3 mm diameter gelatin capsule which was then placed on the substrate and cured with light. The samples were placed in 37° C. $H_2O$ for 24 hours and debonded using an Instron Universal 1011 testing machine using a cross head speed of 1 mm/min.

[1]Bond Strength Standard Test:
Materials and Equipment:
1. Instron Tester
2. Gelatin capsules, #3
3. Five ¼-ounce polycons
4. Bovine teeth
5. Dental model trimmer
6. King Temporary Crown and Bridge Material or any other cold curing acrylic resin
7. Den-Mat designed laboratory curing light
8. Timer
9. Mixing sticks
10. Light-Cured Marathon™ Resin and Powder (Den-Mat Corporation)
11. Bond strength test fixtures ofr Instron Tester
12. Small disposable beakery
13. Water bath
Method:
1. Select 5 large bovine teeth.
2. Using dental model trimmer, grind each tooth to a flat, dentin surface.
3. After all 5 teeth have been ground, remove lids from 5¼-ounce polycons and set aside.
4. Into a small disposable beaker, weigh 5½ grams of Kind Powder (Den-Mat Corporation) and 6 grams of Kind Liquid (Den-Mat Corporation). Mix well with a plastic mixing stick and pour into previously set aside polycon lids until half full.
5. Carefully place tooth into center of polycon lid, taking care not to contaminate flat ground surface. Allow Kind to cure at least to a rubbery consistence.
6. Mix another quantity of Kind and pour into polycon lid until full, taking are again not to contaminate flat ground surface. Allow Kind to cure completely.
7. When all 5 samples have been imbedded and Kind is completely cured, apply material to be tested to ground flat surface, following instructions for that particular product.
8. Fill small diameter half of each of 5 #3 gelatin capsules with Marathon™ mixed to a 3:1 powder/liquid ratio. Apply to prepared tooth surface.
9. Cure each prepared sample in laboratory curing light as follows:
10. place sample at a 30° angle to the perpendicular in center of curing chamber.
11. Turn on curing light for one minute suing timer.
12. Rotate sample 90° and expose for an additional minute.
13. Repeat step c. two more times so that entire 360° of circle has been covered.
14. Mark sample for identification and place in 37° water bath for one hour.
15. Make sure that Instron Tester is configured for bond strength of testing.
16. After 1 hour, remove samples from conditioning water. Using special fixture, stress until failure on Instron at a crosshead speed of 0.02 in/min. Calculations: bond strength=loadatfailure/areaofsample (For #3 gelatin capsules, area of sample is 0.0342 mm.) Average of three highest values is taken as the bond strength.

The following results show the mean bond strengths and standard deviations in megapascals of at least 10 mpa;

hydroxyapatite: 20.9 mpa, $SD^2$, 3.6 mpa;

[2]Standard deviation bone tissue: 7.9 mpa, SD, 2.4 mpa.
   titanium:
     primary coating A=21.3 mpa, SD, 1.94
     primary coating B=24.1 mpa, SD, 2.39

The following shear tests (psi after 24 hours in water) indicate the superior bonding of the primary coating to various dental surfaces suitably for prosthetic device construction.

| | COATING | PORCELAIN | NP METAL | STAINLESS STEEL |
|---|---|---|---|---|
| Study 1 | Primer | 1800 | 1620 | 1270 |
| | Primary A | 2164 | 1421 | 2714 |
| | Primary B | 2438 | 1667 | 2602 |
| Study 2 | Primary A | 3368 | 2292 | 3216 |
| | Primary B | 2719 | 1761 | 2830 |
| Average | Primary A | 2766 | 1857 | 2965 |
| | Primary B | 2679 | 1714 | 2716 |

Primary coating B is a lower viscosity version of primary coating A.

Though this invention has been described with respect to a plurality of details, it is not intended that the invention be limited thereby except to the extent that such limitations appear in the claims. Other embodiments that are obvious variations of the embodiments herein disclosed are intended to be encompassed by this invention.

We claim:

1. In the process of implanting a metal dental prosthesis into or on the alveolar bone, to provide anchorage or stabilization either to a tooth or to another prosthesis, which involves surgical exposure of the alveolar bone, providing means for (a) fixing a metal implant in the alveolar bone, and (b) fixing the metal implant to either a tooth or to the other prosthesis, and closing the exposure of the alveolar bone, the improvement which comprises including in respect to such means the step of applying to one or more portions of the implant or to the locus of the implant in the alveolar bone, a primary coating comprising a crosslinked resin that (i) optionally contains leachable fluoride and (ii) is biocompatible with osseous and non-osseous tissue, to effect direct bonding of the dental prosthesis to the tooth or to the another prosthesis, or to bone or to non-osseous tissue or a combination of them.

2. The process of claim 1 wherein the primary coating is free of leachable fluoride.

3. The process of claim 1 wherein closing the exposure of the alveolar bone is for the purpose of effecting normal healing of the surgically affected site.

4. The process of claim 1 wherein the primary coating comprises
   a) a tenaciously-bonded hydrophilic water insoluble crosslinked resin coating,
   b) that optionally contains a measurable amount of a water/fluid leachable fluoride capable of (a) being leached from the coating in a metered amount, and (b) transporting a small amount of leached fluoride from the coating into the bone and associated soft tissue.

5. The process of claim 4 wherein the implanted dental prosthesis is more stably bonded to the alveolar bone and to associated soft tissue with which the dental prosthesis comes into contact.

6. The process of claim 5 wherein the dental prosthesis is made of one or more of metal, ceramic and plastic.

7. The process of claim 1 wherein the improvement includes the use of a primer coating comprising a strongly adhesively-bonded crosslinkable acrylic resin that possesses less hydrophilicity than the primary coating with or without fluoride.

8. The process of claim 7 wherein the bone, the dental prosthesis, and the another prosthesis each have an external surface, and the primer coating rapidly in situ cures on one or more of an application surface, the bone and prosthetic surface, to function as a primer surface for the primary coating with or without fluoride that is applied to the same surface.

9. The process of claim 1 wherein the primary coating comprises a resin based on an ethylenically unsaturated-functional monomer that contains a hygroscopic group.

10. The process of claim 9 wherein the ethylenically-unsaturated-functional monomer contains hygroscopic groups and exhibits hydrophilicity.

11. In the process of implanting a metal dental prosthesis into or on the alveolar bone, to provide anchorage or stabilization either to a tooth or to another prosthesis, which involves surgical exposure of the alveolar bone, providing means for (a) fixing a metal implant in the alveolar bone, and (b) fixing the metal implant to either a tooth or to the other prosthesis, and closing the exposure of the alveolar bone, the improvement which comprises including in respect to such means the step of applying to one or more portions of the implant or to the locus of the implant in the alveolar bone, a primary coating comprising a crosslinked resin that (i) contains leachable fluoride and (ii) is biocompatible with osseous and non-osseous tissue, to effect direct bonding of the implant to the tooth or to the prosthesis, or to bone or to non-osseous tissue or a combination of them.

12. The process of claim 11 wherein the fluoride is present in the primary coating such that it is leachable from the primary coating over an extended period of time.

13. The process of claim 11 wherein the primary coating comprises a two component blend in which the
   a) first component comprises:
      i) a fluoride source that includes a particulate siliceous fluoride containing filler in which the fluoride is water leachable;
      ii) a coupling agent that includes one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds;
      iii) a photoinitiator; optionally, a radiopaquing agent; and, optionally, a buffering agent; and
   b) second component comprises:
      i) an ethylenically-unsaturated-functional monomer;
      ii) a soft crosslinker that includes one or more of 2,2-bis (4-methacryloxy 2-ethoxyphenyl) propane and diethyleneglycol bismethacrylate;
      iii) a hard crosslinker that includes one or more of (i) the adduct of pyromellitic acid dianhydride and 2-hydroxyethylmethacrylate, (ii) the adduct of 3,3', 4,4'-benzophenonetetracarboxylic dianhydride and 2-hydroxyethylmethacrylate, (iii) 4-methacryloxyethyltrimellitic anhydride, and (iv) other compounds containing at least one group or moiety capable of free radical polymerization and at least one aromatic ring or moiety containing electron withdrawing substituents that do not interfere with free radical polymerization;
      iv) a photoinitiator;
      v) a polymerized carboxylic acid;
      vi) a free-radical scavenger; and
      vii) a curing catalyst.

14. The process of claim 11 wherein the primary coating is a light-curable adhesive composition containing:
   a) a first component comprising:
      i) a fluoride source including a particulate siliceous fluoride containing filler in which the fluoride is water leachable;
      ii) a soft crosslinker;
      iii) an ethylenically-unsaturated-functional monomer;
      iv) a photoinitiator;
      v) a free-radical scavenger;
      vi) a thermal initiator;
      vii) a polymerized carboxylic acid;
      viii) a hard crosslinker including one or more of (i) the adduct of pyromellitic acid dianhydride and 2-hydroxyethylmethacrylate; (ii) the adduct of 3,3', 4,4'-benzophenonetetracarboxylic dianhydride and 2-hydroxyethylmethacrylate, (iii) 4-methacryloxyethyltrimellitic anhydride, and (iv) other compounds containing at least one group or moiety capable of free radical polymerization and at least one aromatic ring or moiety containing electron withdrawing substituents that do not interfere with free radical polymerization, and
   b) a second component comprising:
      i) a fluoride source including a particulate siliceous fluoride containing filler in which the fluoride is water leachable;
      ii) a soft crosslinker;
      iii) an ethylenically-unsaturated-functional monomer;
      iv) a coupling agent including one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds;
      v) a photoinitiator;
      vi) a radiopaquing agent; and
      vii) a buffering agent.

15. The process of claim 11 wherein the primary coating composition contains
   a) a particulate glass having the composition of

| Component | Mole % | Component | Mole % |
|---|---|---|---|
| $SiO_2$ | 17.6–21.6 | $P_2O_5$ | 0.8–3.5 |
| $Al_2O_3$ | 9.0–11.0 | $Na_2O$ | 0.5–3.0 |
| MO | 7.9–19.7 | F | 42.2–56.1 | in which M is an alkaline earth metal and MO is barium oxide and barium oxide binary and ternary mixtures with other alkaline earth metal oxides;

27 b) The alkali metal salt of the adduct of N-(p-tolyl)glycine and glycidyl methacrylate;

c) The adduct of pyromellitic acid dianhydride and 2-hydroxyethyl methacrylate;

d) Ethyl 4-dimethylamino benzoate and camphoquinone (i.e., 2, 3-bornanedione);

e) Ethoxylated bisphenol A dimethacrylate and the adduct of glycidylmethacrylate and bisphenol A, f) 2-hydroxyethyl methacrylate;

g) Butylated hydroxytoluene free radical scavenger h) Polyacrylic acid;

i) Benzoyl peroxide or other peroxide that cause free radical addition at about 55° C. or at a lower temperature.

16. In the process of implanting a metal dental prosthesis into or on the alveolar bone, to provide anchorage or stabilization either to a tooth or to another prosthesis, which involves surgical exposure of the alveolar bone, providing means for (a) fixing a metal implant in the alveolar bone, and (b) fixing the metal implant to either a tooth or to the other prosthesis, and closing the exposure of the alveolar bone, the improvement which comprises including in respect to such means the step of applying to one or more portions of the implant or to the locus of the implant in the alveolar bone, a primary coating comprising a crosslinked resin based on an ethylenically unsaturated-functional monomer that (i) contains a hygroscopic group from the group consisting of hydroxyl, amide, amine, aliphatic ether, hydroxyalkyl amine, hydroxyalkyl amide, pyrrolidone, and ureyl, and exhibits hydrophilicity; (ii) optionally contains leachable fluoride and (iii) is biocompatible with osseous and non-osseous tissue, to effect direct bonding of the implant to the tooth or to the prosthesis, or to bone or to non-osseous tissue or a combination of them.

17. The process of claim 16 wherein the primary coating contains a polycarboxylic acid.

18. The process of claim 17 wherein the polycarboxylic acid is in the form of its alkali metal salt.

19. The process of claim 17 wherein the primary coating contains a variety of crosslinking agents.

20. The process of claim 19 wherein one crosslinking agent is a hard crosslinker and another is a soft crosslinker.

21. The process of claim 20 wherein each hard and soft crosslinker is a polyfunctional molecule in which the functionality is complementary to the ethylenic unsaturation of the ethylenically-unsaturated-functional monomer.

22. The process of claim 21 wherein in the hard crosslinker, the functional groups are bonded via an aliphatic group of up to 10 carbon atoms, to a central moiety that is aromatic in nature.

23. The process of claim 22 wherein the hard crosslinkers raise the $T_g$ of the cured primary coating.

24. The process of claim 21 wherein the soft crosslinker contains the functional groups bonded to a central moiety that comprises a group that has the flexibility of an alkane or contains arkyl benzene.

25. The process of claim 24 where the flexible groups are the residues of ethylene glycol, diethylene glycol, 2,2-bis (4-hydroxyphenyl)propane, or 2,2,-bis(4-hydroxyphenyl) fluorinated alkanes.

26. The process of claim 19 wherein the primary coating contains a coupling agent.

27. The process of claim 26 wherein the coupling agent is functionally complementary to the ethylenically-unsaturated-functional monomer.

28. The process of claim 27 wherein the coupling agent contains a functional group that is reactable with the ethylenic unsaturation.

28

29. The process of claim 28 wherein the functional group is an acrylic-type ethylenic unsaturation.

30. The process of claim 27 wherein the coupling agent includes a surface bonding group that can impart one or more properties to the primary coating:

a) chemical bonding capabilities to a substrate surface to which the primary coating is applied; and b) wetting agent properties in that it reduces the surface tension of the coating, causing the coating to spread across or penetrate more easily the surface of the substrate onto which the primary coating is applied.

31. In the process of implanting a metal dental prosthesis into or on the alveolar bone, to provide anchorage or stabilization either to a tooth or to another prosthesis, which involves surgical exposure of the alveolar bone, providing means for (a) fixing a metal implant in the alveolar bone, and (b) fixing the metal implant to either a tooth or to the other prosthesis, and closing the exposure of the alveolar bone for the purpose of effecting normal healing of the surgically affected site, the improvement which comprises including in respect to such means the step of applying to one or more portions of the implant or to the locus of the implant in the alveolar bone, a primary coating comprising a crosslinked resin that (i) contains at least one of a free-radical catalytic curing agent and a free-radical photoinitiator, (ii) optionally contains leachable fluoride and (iii) is biocompatible with osseous and non-osseous tissue, to effect direct bonding of the implant to the tooth or to the prosthesis, or to bone or to non-osseous tissue or a combination of them.

32. The process of claim 31 wherein the primary coating contains a free-radical catalytic curing agent and a free-radical photoinitiator, and the coating can be cured by each of them.

33. In the process of implanting a metal dental prosthesis into or on the alveolar bone, to provide anchorage or stabilization either to a tooth or to another prosthesis, which involves surgical exposure of the alveolar bone, providing means for (a) fixing a metal implant in the alveolar bone, and (b) fixing the metal implant to either a tooth or to the other prosthesis, and closing the exposure of the alveolar bone, the improvement which comprises including in respect to such means the steps of applying to one or more portions of the implant or to the locus of the implant in the alveolar bone, a primary coating comprising a crosslinked resin that (i) optionally contains leachable fluoride and (ii) is biocompatible with osseous and non-osseous tissue, to effect direct bonding of the implant to the tooth or to the prosthesis, or to bone or to non-osseous tissue or a combination of them, and using a primer coating comprising a strongly adhesively-bonded crosslinkable acrylic resin that possesses less hydrophilicity than the primary coating with or without fluoride, the primer coating involves a two part (package) composition, further comprising (a) a compound selected from the group consisting of (1) N-phenylglycine, (2) the adduct of N-(p-tolyl) glycine and glycidyl methacrylate, (3) the addition reaction product of N-phenylglycine and glycidyl methacrylate, (4) N-(p-tolyl) glycine, N-phenylalanine, sarkosine, N-lauroylsarkosine, glycine, N,N-dimethyl-glycine, 3-(N-phenyl) amino propionic acid, 3-(N-p-tolyl) amino propionic acid, omega-amino fatty acids, N-substituted-omega-amino fatty acids, and other amino acids; in which each member of the group of (1), (2), (3) and (4) that is present in the solution is an alkali metal salt form of that member, and (b) a composition comprising at least one monomer selected from the group consisting of (1) the addition reaction product of pyromellitic acid dianhydride and 2-hydroxyethyl methacrylate, (2) the addition reaction product of 3,3', 4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization.

34. The process of claim 33 wherein the primer coating is applied to a surface of either the dental prosthesis, the alveolar bone, the tooth, or the another prosthesis or a combination of them according to the steps of (a) first contacting the surface with an aqueous solution comprising at least one strong acid or acidic salt in order to condition the surface, (b) then contacting the surface with a solution comprising a solvent and at least one compound selected from the group consisting of (1) N-phenylglycine, (2) the adduct of N-(p-tolyl)glycine and glycidyl methacrylate, (3) the addition reaction product of N-phenylglycine and glycidyl methacrylate, and (4) other amino acids, in which each member of the group of (1), (2), (3) and (4) that is present in the solution is an alkali metal salt form of that member, heating the surface to remove the solvent or maintain the surface at ambient temperature until the solvent is evaporated, and (c) then contacting the surface with a solution comprising at least one monomer selected from the group consisting of (1) the addition reaction product of pyromellitic acid dianhydride and 2-hydroxyethyl methacrylate, (2) the addition reaction product of 3,3', 4,4'-benzophenone tetracarboxylic dianhydride and 2-hydroxyethyl methacrylate, (3) 4-methacryloxyethyltrimellitic-anhydride, and (4) other compounds containing at least one group or moiety capable of free radical polymerization and at least one aromatic ring or moiety containing electron-withdrawing substituents that do not interfere with free radical polymerization, (d) heating the surface to remove residual solvent or maintain the surface at ambient temperature until the solvent is evaporated from the primer coating and the coating is fully reacted.

* * * * *